United States Patent
Peters, Jr.

(10) Patent No.: US 9,561,091 B2
(45) Date of Patent: Feb. 7, 2017

(54) TOOTHPICK DEVICE

(76) Inventor: Cassie Peters, Jr., Phoenix, AZ (US)

( * ) Notice: Subject to any disclaimer, the term of this patent is extended or adjusted under 35 U.S.C. 154(b) by 584 days.

(21) Appl. No.: 11/699,239

(22) Filed: Jan. 29, 2007

(65) Prior Publication Data

US 2008/0178904 A1   Jul. 31, 2008

Related U.S. Application Data

(63) Continuation-in-part of application No. 10/958,084, filed on Oct. 4, 2004, now abandoned.

(51) Int. Cl.
  *A61C 15/00* (2006.01)
  *A61C 15/02* (2006.01)
  *A61C 15/04* (2006.01)

(52) U.S. Cl.
  CPC ............. *A61C 15/02* (2013.01); *A61C 15/041* (2013.01); *A61C 15/046* (2013.01)

(58) Field of Classification Search
  CPC ....... A61C 15/00; A61C 15/02; A61C 15/041; A61C 15/046

USPC .... 132/321, 323, 324, 328, 329; D28/65, 66
See application file for complete search history.

(56) References Cited

U.S. PATENT DOCUMENTS

| | | | | |
|---|---|---|---|---|
| 407,362 | A * | 7/1889 | Mason | 132/321 |
| 2,702,555 | A * | 2/1955 | De Mar Michael | 264/249 |
| 3,838,702 | A * | 10/1974 | Standish et al. | 132/321 |
| 4,403,625 | A * | 9/1983 | Sanders et al. | 132/323 |
| 4,852,728 | A * | 8/1989 | Court | 206/63.5 |
| 5,680,875 | A * | 10/1997 | Winters | 132/324 |
| 5,915,392 | A * | 6/1999 | Isaac | 132/200 |
| 6,102,051 | A * | 8/2000 | Neves | 132/321 |

* cited by examiner

*Primary Examiner* — Rachel Steitz
(74) *Attorney, Agent, or Firm* — Venjuris, P.C.

(57) ABSTRACT

A toothpick device for cleaning teeth includes a toothpick. The toothpick is comprised of two separable portions and has at least one pointed end. A length of dental floss is provided with each end of the dental floss being secured to one of the two portions of the toothpick by melted wax. The dental floss is wound for storage between said two portions whereby separating the two portions unwinds the dental floss for use.

6 Claims, 1 Drawing Sheet

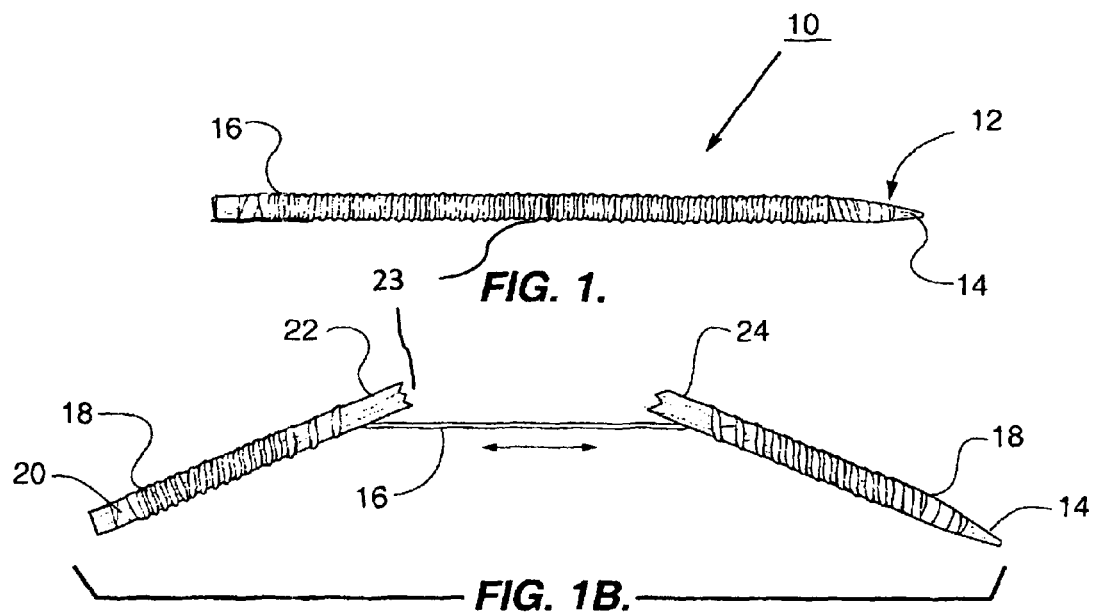
FIG. 1.
FIG. 1B.
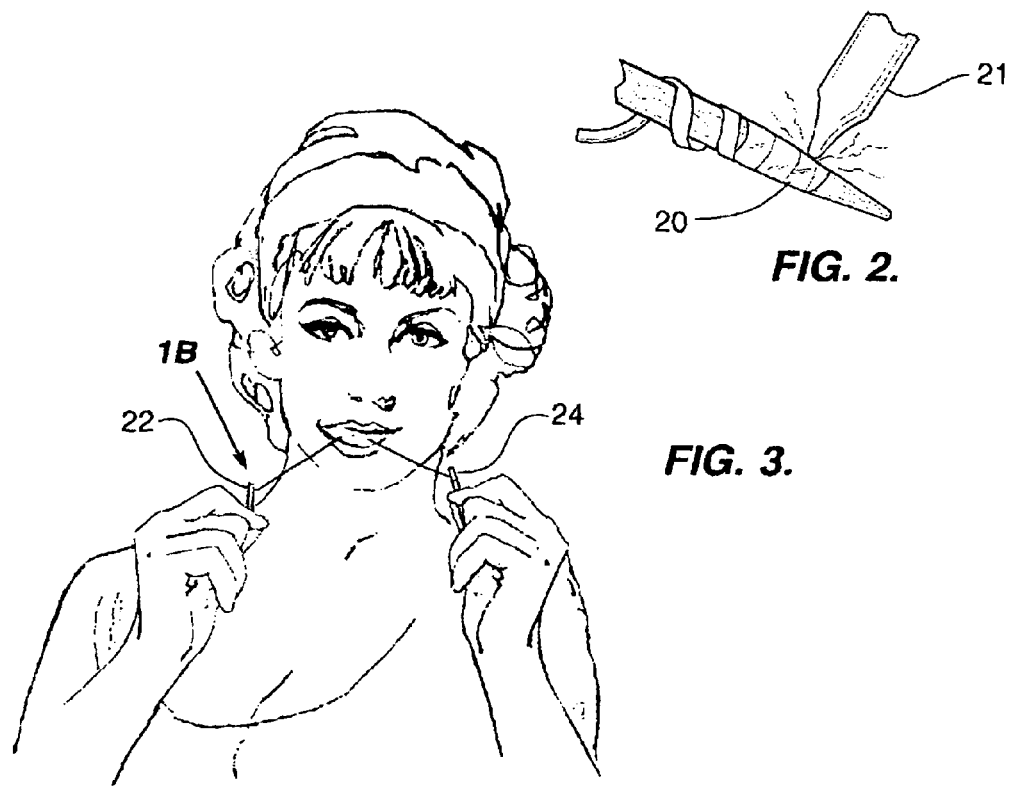
FIG. 2.
FIG. 3.

TOOTHPICK DEVICE

RELATED APPLICATION

This is a continuation-in-part of co-pending patent application Ser. No. 10/958,084 filed Oct. 4, 2004.

TECHNICAL FIELD

This invention relates generally to the field of toothpicks, and, more particularly, to an improved toothpick and floss combination.

BACKGROUND OF THE INVENTION

Dental floss is a mainstay of care for the teeth. The American Dental Association (ADA) recommends brushing twice a day and cleaning between the teeth with floss or interdental cleaners once each day to remove plaque from all tooth surfaces. Plaque is responsible for both tooth decay and gum disease. Floss helps remove food debris caught between teeth that may not be rinsed or brushed away.

However, when away from the home, the majority of individuals do not carry floss for dental care. Instead, to remove food debris from between the teeth, persons often use toothpicks which are ubiquitous in restaurants across the United States. However, while toothpicks are useful for the larger food debris, it is not very satisfactory for smaller food debris which may not even be felt. In addition, reaching between back teeth such as molars is very difficult with a toothpick. Thus, there is a need for a device to make floss as common as toothpicks for individual use.

United Kingdom GB 2289845 entitled "Toothpick Containing Dental Floss" which published on Dec. 6, 1995 filed by Lara provides a breakable toothpick containing dental floss.

U.S. Pat. No. 6,102,051 entitled "Flossing Kit" which issued on Aug. 15, 2000 to Neves shows a toothpick containing a supply of dental floss wrapped about one end. Neves leaves one end of said floss free.

U.S. Pat. No. 4,633,892 entitled "Oral Hygiene Device" which issued on Jan. 6, 1987 to Charatan discloses an oral hygiene device comprising a hollow housing (not a toothpick) containing dental floss which may be broken into two portions which serve as handles for manipulating the floss.

U.S. Pat. No. 5,253,661 entitled "Composite Oral Cleaning Device" which issued on Oct. 19, 1993 to Alonzo has an oral cleaning apparatus with one pointed tip and a spool or cleat region suitable for wrapping and holding a supply of dental floss. The floss is not attached to the device except for winding around said apparatus.

U.S. Pat. No. 4,852,728 entitled "Oral Hygiene Device" which issued on Aug. 1, 1989 to Court discloses a disposable single use packet having first and second members releasably attached to one another with a sanitary interior compartment containing floss.

U.S. Pat. No. 4,403,625 entitled "Disposable Buccal Hygenic Device" which issued on Sep. 13, 1983 to Sanders et al. shows floss contained within an interior cavity of a device.

German Patent No. DE 199 44 321 A1 to Rauschenberg discloses a two piece toothpick having floss wrapped around the exterior thereof which is separable. Rauschenberg attaches the floss by drilling holes in the toothpick to attach thereto.

There are a number of issues regarding the use of toothpicks themselves to provide floss for use in restaurants. First, as shown in the art cited below, most devices store the floss internally. Creating such a cavity in a standard toothpick, given the wood material used in toothpicks and the relatively small diameter thereof, would be extremely difficult. To store the floss externally results in problems with breakage of the toothpick to release said floss since the wood material of a standard toothpick tends to splinter when broken. Lastly, the attachment of floss via drilling holes in the standard toothpick causes an extra manufacturing step to make such a device workable. In addition, those holes tend to weaken the structure of the toothpick causing breakage. The present invention overcomes these issues.

None of the known prior art disclose the combination set forth herein.

SUMMARY OF THE INVENTION

It is an object of this invention to provide an improved toothpick in combination with dental floss.

It is an further object of this invention to provide an improved toothpick and floss combination which is easily to use and convenient.

Further objects and advantages of the invention will become apparent as the following description proceeds and the features of novelty which characterize this invention will be pointed out with particularity in the claims annexed to and forming a part of this specification.

BRIEF DESCRIPTION OF THE DRAWINGS

The present invention may be more readily described by reference to the accompanying drawings in which:

FIG. 1 is a side view of one embodiment of a toothpick and floss combination of the present invention;

FIG. 1B is a side view of the embodiment of FIG. 1 showing the toothpick broken to dispense floss therefrom;

FIG. 2 is a close up view of the circled area of FIG. 1B; and

FIG. 3 is a perspective view of the embodiment of FIG. 2 in use by a woman.

DESCRIPTION OF THE PREFERRED EMBODIMENT

A toothpick device for cleaning teeth includes a toothpick and a length of waxed dental floss 16. The toothpick is comprised of two separable portions and has at least one pointed end. The length of waxed dental floss 16 is provided with each end of waxed dental floss 16 being secured to one of the two portions of the toothpick melted wax. The dental floss is wound for storage between said two portions whereby separating the two portions unwinds the dental floss for use.

Referring more particularly to the drawings by characters of reference, FIGS. 1-2 disclose combinations of features which constitute the components of one embodiment of a toothpick device 10 of the present invention. In the presently preferred embodiment, toothpick device 10 comprises a toothpick 12 having a pointed end 14. The length of dental floss 16 is wound about the exterior of toothpick 12. This avoids a need for an internal cavity for storage of floss 16.

To secure both ends 18 of dental floss 16 to toothpick 12, said ends 18 are wound over one another as best seen in FIG. 2. A heating element 21 is brought into close proximity to ends 18, close enough and hot enough to melt the wax from the waxed dental floss 16. The melted was flows onto the toothpick and, upon withdrawal of heating element 21, resolidifies thereby affixing ends 18 to said toothpick.

In use, the user may use point 14 to larger particles of food debris from between his or her teeth in a manner well known in the art. When flossing is desired, the user simply breaks toothpick 12 thereby creating the separable portions which are blunt toothpick half 22 and pointed toothpick half 24 as shown in FIG. 1B. To facilitate breakage at the mid-point of said toothpick 12, said toothpick may have score lines 23. As blunt toothpick half 22 and pointed toothpick half 24 are separated, dental floss 16 unwinds for use. As best seen in FIG. 3, each half 20 and 22 acts as a handle while dental floss 16 is applied to the user's teeth.

Those skilled in the art will recognize the advantage of this invention which employs off standard wooden toothpick 12 and a simple length of standard waxed dental floss. There is no adhesive, no other needed elements whereby manufacturing same is simple and straight forward. In addition, the wrappage of floss 16 around toothpick 12 prevents splintering of the toothpick when broken as described above.

Further, those skilled in the art will recognize that the embodiments discussed herein can be packaged in many different ways. For example, said devices 10 can be packaged in individual glassine envelopes or simply provided in bulk in dispensers or boxes as desired.

Although only certain embodiments have been illustrated and described, it will be apparent to those skilled in the art that various changes and modifications may be made therein without departing from the spirit of the invention or from the scope of the appended claims.

What is claimed is:

1. A toothpick device for cleaning teeth, comprising:
a toothpick having an exterior surface; the exterior surface comprising a floss-wrapping region that is substantially smooth and free from manufactured notches and free from manufactured indentations;
a piece of waxed dental floss comprising a length of dental floss having opposed first and second ends and coated with wax from the first end of the length of dental floss to the second end of the length of dental floss, the length of dental floss wrapped around the exterior surface of the toothpick from the first end of the length of dental floss to the second end of the length of dental floss; and
the wax of the piece of waxed dental floss at the first and second ends of the length of dental floss melted and resolidified with respect to the exterior surface of the toothpick forming melted and resolidified wax of the wax of the piece of waxed dental floss between the first and second ends of the length of dental floss and the exterior surface of the toothpick securing the first and second ends of the length of dental floss to the floss-wrapping region of the exterior surface of the toothpick;
whereby a user of the toothpick device can divide the toothpick into parts so that the user can hold one part of the divided toothpick in each hand and floss the user's teeth with the floss between the parts of the divided toothpick.

2. A toothpick device according to claim 1, wherein the toothpick is fashioned of wood.

3. A toothpick device for cleaning teeth, comprising:
a toothpick having an exterior surface; the exterior surface being substantially smooth and free from manufactured notches and free from manufactured indentations:
a piece of waxed dental floss comprising a length of dental floss having opposed first and second ends and coated with wax from the first end of the length of dental floss to the second end of the length of dental floss, the length of dental floss wrapped around the exterior surface of the toothpick from the first end of the length of dental floss to the second end of the length of dental floss;
the wax of the piece of waxed dental floss at the first and second ends of the length of dental floss melted and resolidified with respect to the exterior surface of the toothpick forming melted and resolidified wax of the wax of the piece of waxed dental floss between the first and second ends of the length of dental floss and the exterior surface of the toothpick securing the first and second ends of the length of dental floss to the exterior surface of the toothpick; and
the toothpick is separable between the first and second ends of the length of dental floss to form two separate portions of the toothpick, and separating the two separate portions of the toothpick unwinds the piece of waxed dental floss from the exterior surface of the toothpick from the two separate portions of the toothpick between the first and second ends of the length of dental floss.

4. A toothpick device according to claim 3, wherein the toothpick is fashioned of wood.

5. A method, comprising:
providing a toothpick having an exterior surface; the exterior surface comprising a floss-wrapping region that is substantially smooth and free from manufactured notches and free from manufactured indentations;
providing a piece of waxed dental floss comprising a length of dental floss having opposed first and second ends and coated with wax from the first end to the second end;
wrapping the piece of waxed dental floss around the exterior surface of the toothpick from the first end of the length of dental floss to the second end of the length dental floss;
melting and resolidifying the wax of waxed dental floss between the first end of the length of dental floss and the exterior surface of the toothpick to form melted and resolidified wax of the wax of the waxed dental floss between the first end of the length of dental floss and the exterior surface of the toothpick securing the first end of the length of dental floss to the exterior surface of the toothpick; and
melting and resolidifying the wax of the waxed dental floss between the second end of the length of dental floss and the exterior surface of the toothpick to form melted and resolidified wax of the wax of the waxed dental floss between the second end of the length of dental floss and the exterior surface of the toothpick securing the second end of the length of dental floss to the floss-wrapping region of the exterior surface of the toothpick.

6. The method according to claim 5, further comprising:
breaking the toothpick between the first end of the length of dental floss and the second end of the length of dental floss to form two separate portions of the toothpick; and
separating the two separate portions unwinding the piece of waxed dental floss with respect to the two separate portions between the first and second ends of the length of dental floss.

* * * * *